(12) United States Patent
Hall et al.

(10) Patent No.: US 8,951,892 B2
(45) Date of Patent: Feb. 10, 2015

(54) APPLICATIONS FOR NANOPILLAR STRUCTURES

(75) Inventors: Mark D. Hall, Austin, TX (US); Mehul D. Shroff, Austin, TX (US)

(73) Assignee: Freescale Semiconductor, Inc., Austin, TX (US)

( * ) Notice: Subject to any disclaimer, the term of this patent is extended or adjusted under 35 U.S.C. 154(b) by 0 days.

(21) Appl. No.: 13/539,070

(22) Filed: Jun. 29, 2012

(65) Prior Publication Data

US 2014/0001432 A1  Jan. 2, 2014

(51) Int. Cl.
| | | |
|---|---|---|
| H01L 21/02 | (2006.01) | |
| H01L 29/66 | (2006.01) | |
| B82Y 40/00 | (2011.01) | |

(52) U.S. Cl.
USPC ...... 438/478; 257/9; 257/E29.166; 257/E21.002; 977/932

(58) Field of Classification Search
CPC .......................... H01L 29/0673; H01L 29/0676
USPC .............................................. 257/9; 438/478
See application file for complete search history.

(56) References Cited

U.S. PATENT DOCUMENTS

| | | |
|---|---|---|
| 6,645,444 B2 | 11/2003 | Goldstein |
| 6,646,302 B2 | 11/2003 | Kan et al. |
| 6,743,709 B2 | 6/2004 | Kan et al. |
| 6,919,046 B2 | 7/2005 | O'Connor et al. |
| 7,205,096 B2 | 4/2007 | Park et al. |
| 7,309,467 B2 | 12/2007 | Chen et al. |
| 7,338,554 B2 | 3/2008 | Delaunay et al. |
| 7,393,746 B2 | 7/2008 | Dyer et al. |
| 7,432,158 B1 * | 10/2008 | Rao et al. ............... 438/264 |
| 7,670,831 B2 | 3/2010 | Lee et al. |
| 7,683,438 B2 | 3/2010 | Jeng |
| 7,780,758 B2 | 8/2010 | Park et al. |
| 7,799,634 B2 | 9/2010 | Shen et al. |
| 7,833,801 B2 | 11/2010 | Stasiak et al. |
| 7,919,786 B2 | 4/2011 | Jin et al. |
| 8,097,873 B2 | 1/2012 | Muralidhar et al. |
| 8,110,510 B1 | 2/2012 | Fanfair et al. |
| 2002/0061646 A1 | 5/2002 | Kan et al. |
| 2002/0192949 A1 | 12/2002 | Kan et al. |
| 2003/0008145 A1 | 1/2003 | Goldstein et al. |
| 2004/0043583 A1 | 3/2004 | Rao et al. |
| 2005/0265935 A1 | 12/2005 | Hollingsworth et al. |

(Continued)

OTHER PUBLICATIONS

Chang, Ting-Chang, Jian, Fu-Yen, Chen, Shih-Cheng, and Tsai, Yu-Ting, Developments in Nanocrystal Memory, MaterialsToday, Dec. 2011, vol. 14, No. 12, pp. 608-615.

(Continued)

*Primary Examiner* — Kimberly Rizkallah
*Assistant Examiner* — Mounir Amer

(57) ABSTRACT

A disclosed method of fabricating a hybrid nanopillar device includes forming a mask on a substrate and a layer of nanoclusters on the hard mask. The hard mask is then etched to transfer a pattern formed by the first layer of nanoclusters into a first region of the hard mask. A second nanocluster layer is formed on the substrate. A second region of the hard mask overlying a second region of the substrate is etched to create a second pattern in the hard mask. The substrate is then etched through the hard mask to form a first set of nanopillars in the first region of the substrate and a second set of nanopillars in the second region of the substrate. By varying the nanocluster deposition steps between the first and second layers of nanoclusters, the first and second sets of nanopillars will exhibit different characteristics.

9 Claims, 5 Drawing Sheets

(56) References Cited

U.S. PATENT DOCUMENTS

| | | |
|---|---|---|
| 2005/0271815 A1 | 12/2005 | Delaunay et al. |
| 2006/0068026 A1 | 3/2006 | Hu et al. |
| 2006/0076609 A1 | 4/2006 | Chindalore et al. |
| 2006/0110686 A1 | 5/2006 | Park et al. |
| 2006/0220102 A1 | 10/2006 | Mathew et al. |
| 2007/0004146 A1 | 1/2007 | Prinz et al. |
| 2007/0018207 A1 | 1/2007 | Prinz |
| 2007/0018216 A1 | 1/2007 | Chindalore et al. |
| 2007/0018221 A1 | 1/2007 | Swift et al. |
| 2007/0018222 A1 | 1/2007 | Sadd et al. |
| 2007/0018229 A1 | 1/2007 | Yater et al. |
| 2007/0018232 A1 | 1/2007 | Chindalore et al. |
| 2007/0018234 A1 | 1/2007 | Chindalore et al. |
| 2007/0018240 A1 | 1/2007 | Chindalore et al. |
| 2007/0019472 A1 | 1/2007 | Yater et al. |
| 2007/0020820 A1 | 1/2007 | Chindalore et al. |
| 2007/0020831 A1 | 1/2007 | Chindalore et al. |
| 2007/0020840 A1 | 1/2007 | Chindalore et al. |
| 2007/0020845 A1 | 1/2007 | Swift et al. |
| 2007/0020849 A1 | 1/2007 | Hong et al. |
| 2007/0020851 A1 | 1/2007 | Hong et al. |
| 2007/0020856 A1 | 1/2007 | Sadd et al. |
| 2007/0020857 A1 | 1/2007 | Chindalore et al. |
| 2007/0054452 A1 | 3/2007 | Hong et al. |
| 2007/0072318 A1 | 3/2007 | Hwang et al. |
| 2007/0082449 A1 | 4/2007 | Chindalore |
| 2007/0082495 A1 | 4/2007 | Mathew et al. |
| 2007/0089564 A1 | 4/2007 | Tung |
| 2007/0105306 A1 | 5/2007 | Prinz et al. |
| 2007/0105307 A1 | 5/2007 | Jeng |
| 2007/0126076 A1 | 6/2007 | Mathew et al. |
| 2007/0205421 A1 | 9/2007 | Mathew et al. |
| 2007/0238249 A1 | 10/2007 | Swift et al. |
| 2007/0242534 A1 | 10/2007 | Gasquet |
| 2007/0264574 A1 | 11/2007 | Kim et al. |
| 2007/0287288 A1 | 12/2007 | Park et al. |
| 2008/0019178 A1 | 1/2008 | Yater |
| 2008/0105945 A1 | 5/2008 | Steimle et al. |
| 2008/0173921 A1 | 7/2008 | Li et al. |
| 2008/0173922 A1 | 7/2008 | Hong et al. |
| 2008/0173923 A1 | 7/2008 | Li et al. |
| 2008/0217683 A1 | 9/2008 | Jeng |
| 2008/0242022 A1 | 10/2008 | Rao et al. |
| 2009/0085024 A1* | 4/2009 | Muralidhar et al. ............. 257/4 |
| 2009/0170262 A1 | 7/2009 | Swift et al. |
| 2010/0009432 A1 | 1/2010 | Lee et al. |
| 2010/0096686 A1 | 4/2010 | Li et al. |
| 2010/0155824 A1 | 6/2010 | Hong et al. |
| 2011/0073936 A1 | 3/2011 | Hong et al. |
| 2011/0120100 A1 | 5/2011 | Yin et al. |
| 2011/0255357 A1 | 10/2011 | Pelley, III et al. |
| 2012/0091431 A1 | 4/2012 | Fanfair et al. |
| 2013/0320284 A1 | 12/2013 | Zhou et al. |

OTHER PUBLICATIONS

Mark, S., et al., "Thin Film Processing Using S-Layer Proteins: Biotemplated Assembly of Colloidal Gold Etch Masks for Fabrication of Silicon Nanopillar Arrays", Colloids and Surfaces B: Biointerfaces, vol. 57, Issue 2, Jun. 15, 2007, pp. 161-173.

Smirnov, W. et al., "Aligned Diamond Nano-Wires: Fabrication and Characterisation for Advanced Applications in Bio- and Electrochemistry", Diamond and Related Materials, vol. 19, Issues 2-3, Feb.-Mar. 2010, pp. 186-189.

Wu, B. et al., "High Aspect Ratio Silicon Etch: A Review", Journal of Applied Physics, vol. 108, Issue 5, pp. 051101-1-051101-20 (20 pages), published Sep. 9, 2010.

* cited by examiner

APPLICATIONS FOR NANOPILLAR STRUCTURES

BACKGROUND

1. Field

Disclosed subject matter is in the field of semiconductor devices and, more particularly, devices employing semiconductor fabrication technology to incorporate nanopillars for various applications.

2. Related Art

A nanopillar is a nano-column structure typically formed on a substrate. Nanopillars can be fabricated by forming nanoclusters and using the nanocluster layer as a mask for etching the underlying substrate. See, e.g., R. Muralidhar et al., *Phase Change Memory Structures*, U.S. Pat. No. 8,097,873, (Jan. 17, 2012); C. Hong, *Nanocrystal Memory with Differential Energy Bands and Method of Formation*, U.S. Pat. Pub. No. 2011/0073936 A1, (Mar. 31, 2011); L. Mathew et al., *Semiconductor Device Having Nano-Pillars and Method Therefor*, (Apr. 12, 2007); U.S. App. Pat. Pub. No. 2007/0082495; and F. Zhou, *Field Focusing Features in a Reram Cell*, U.S. patent application Ser. No. 13/486,641, each of which is commonly assigned with the present application and each of which is incorporated herein by reference in its entirety.

BRIEF DESCRIPTION OF THE DRAWINGS

The present invention is illustrated by way of example and is not limited by the accompanying figures, in which like references indicate similar elements. Elements in the figures are illustrated for simplicity and clarity and have not necessarily been drawn to scale.

FIG. 16 depicts a flexible top layer for a pressure gauge or the like;

DETAILED DESCRIPTION

Figure 1:
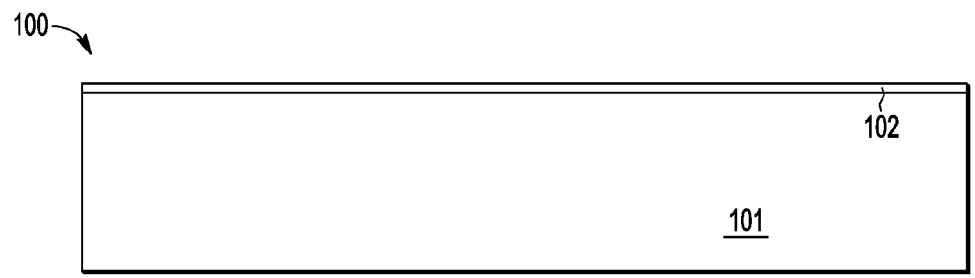
FIG. 1 shows a hard mask over a substrate (e.g., silicon, SOI, III-V)

In one aspect, a disclosed method of fabricating a hybrid nanopillar device includes forming a hard mask layer on a substrate and forming a first layer of nanoclusters on the hard mask. A nanocluster is a discrete structure, typically having a diameter or thickness in the range of 2 to 20 nm, made of a dielectric, a semiconductor, or a metal. A layer of photoresist is then patterned over the first layer of nanoclusters to open a window overlying a first region of the substrate. Using the patterned photoresist and the first set of nanoclusters as an etch mask, a first region of the hard mask layer overlying the first region of the substrate is etched to transfer a pattern formed by the first layer of nanoclusters into the first region of the hard mask layer.

A second set of nanoclusters is then formed on the substrate and a second layer of photoresist is patterned over the second set of nanoclusters to open a window overlying a second region of the substrate. Using the second layer of photoresist and the second set of nanoclusters as an etch mask, a second region of the hard mask layer overlying the second region of the substrate is etched to transfer a pattern formed by the second set of nanoclusters into the second portion of the hard mask layer.

The substrate is then etched through the hard mask layer to form a first set of nanopillars in the first region of the substrate and a second set of nanopillars in the second region of the substrate. By varying the nanocluster deposition steps between the first and second layers of nanoclusters, the first and second sets of nanopillars can be made to have different characteristics such as nanopillar density and average diameter.

The substrate could be a silicon on insulator (SOI) substrate that includes an insulating layer such that the bases of the nanopillars are attached to silicon dioxide or another dielectric. A top plate may be bonded or otherwise formed overlying the open ends of the nanopillars. The top plate could be a bonded silicon layer that may provide electrical continuity among each of the nanopillars in a given nanopillar region. In other embodiments, a glass plate could be bonded to the top of the nanopillars to provide electrical isolation at the top of the nanopillars for applications that might require an applied voltage but no current flow including, as an example, an electrostatic filter application.

The nanoclusters can be of various materials including, as examples, metal, polycrystalline silicon, and dielectric nanoclusters such as silicon dioxide nanoclusters and silicon nitride nanoclusters. Various materials may be used for the hard mask layer as well, depending upon the material used for the nanocrystals. If the nanoclusters are metal, for example, the hard mask layer may be a silicon dioxide-based compound. If the nanoclusters are polysilicon, the nanoclusters may be oxidized to form oxide nanoclusters or nanoclusters with oxide shells and the hard mask layer may be silicon nitride or another material that can be etched selectively with respect to an oxide. Similarly, the hard mask layer material should exhibit high etch selectivity with respect to the substrate material, which may be a doped or intrinsic semiconductor such as silicon.

After nanopillars are formed, a dielectric or other type of filler may be deposited to fill the gaps or voids surrounding each nanopillar. If the deposition of the filler is controlled to leave the upper extremities of the nanopillars exposed or if the filler dielectric is etched back or otherwise recessed, an epitaxial film may be grown using the exposed portions of the nanopillars as seeds for the epitaxial layer. The epitaxial silicon layer could provide a single conducting layer for joining the nanopillars.

The hybrid nanopillar device may be suitable for use in a variety of applications. A flexible and electrically conductive top plate may be formed overlying one or both of the nanopillar regions to implement a piezoresistive sensor that could be used, for example, as a pressure gauge.

A current could be forced through the nanopillars to heat them. Heat could modulate certain reactions in a biological or chemical sensor. Channels or waveguides may be etched into the substrate to provide conduits for fluid, light, or sound. In the case of light signals, the nanopillars could be used to attenuate an incoming light signal. Similarly, rows of closely spaced nanopillar regions could be used to polarize the light to varying degrees.

If sound is provided to the nanopillars through the conduits, nanopillar vibrations could be detected as piezoresistance changes and the vibrations could be converted into electrical signals that could, for example, drive a hearing aid.

If a top plate is bonded or otherwise formed overlying the nanopillars, a voltage could be applied across the top plate and a bottom plate. An applied voltage of a desired polarity could be employed to provide an electrostatic filter.

The nanopillars could be coated with reactive agents to enable biological or chemical sensing. The nanopillars could be formed from a ferromagnetic material. Magnetic nanopillars would enable a magnetic fluid filter.

The nanopillars could be selectively doped so that, for example, a lower portion of a nanopillar could be p-type while an upper portion could be n-type (or vice versa) to produce a p-n junction that might be used for a light-emitting diode structure. In this case, the gaps surrounding the nanopillars might be filled with a phosphor to provide a desired color of light.

In some embodiments, the tops of the nanopillars might be left unattached with no top plate. In these embodiments, the nanopillar structure could be used in biological or chemical sensors that need to be open to the ambient, for example, an air quality monitor.

Because the nanopillars may be fabricated in a semiconductor substrate using semiconductor device fabrication techniques, semiconductor circuitry may be fabricated into the substrate to augment the function or functions provided by the nanopillars.

In another aspect, a hybrid nanopillar device includes a substrate having multiple sets of nanopillars as well as a first device element to provide a signal to the nanopillars, a second device element to monitor a characteristic of the nanopillars, or both. The multiple sets of nanopillars may include a first set located in a first substrate region and a second set located in a second region. The first and second sets of nanopillars may have different characteristics such as different nanopillar densities, different average nanopillar diameters, and so forth. The device element to provide a signal may provide electrical or mechanical signals to the nanopillars. The device elements could provide sound, light, environmental air, fluids, and other media to the nanopillar structures. The device elements to monitor the nanopillars may monitor the temperature, resistivity, motion, frequency, vibrations, or other characteristics of the nanopillars.

Turning now to the drawings, FIG. 1 through FIG. 11 depict selected stages in one embodiment of a fabrication process for forming a hybrid nanopillar device. The hybrid nanopillar device is suitable for use in a variety of applications described in greater detail in the figures that follow FIG. 10 and FIG. 11. As depicted in FIG. 1-FIG. 10, the hybrid nanopillar device includes two or more regions of nanopillar structures where the nanopillar structures in one of the regions differ in one or more characteristics from the nanopillars in the other regions.

The nanopillar regions in the disclosed embodiments may be used for a variety of devices that are integrated within solid-state circuits. These nanopillar based structures may include, for example, filters, sensors, light emitting devices, light attenuating and polarizing devices, sound detection and generation devices including hearing aid devices, devices for detecting biological or chemical agents, and piezoresistance monitoring devices, all of which are fabricated on a nanoscale.

Referring now to FIG. 1, a first stage in one embodiment of a process suitable for fabricating hybrid nanopillar devices is depicted. In the depicted embodiment, FIG. 1 depicts a structure 100 in which a hard mask layer 102 has been formed overlying a substrate 101. Substrate 101 may include a conventional monocrystalline semiconductor substrate such as a crystalline silicon substrate. In other embodiments, substrate 101 may be an SOI substrate that includes an insulating layer, such as a buried oxide layer, formed in the substrate bulk. Substrate 101 may include one or more layers of epitaxial films formed overlying a bulk portion of substrate 101. Similarly, substrate 101 may include heavily and lightly doped n-type regions, heavily and lightly doped p-type regions, insulating regions, and so forth. Substrate 101 may comprise a portion of a semiconductor wafer that is not depicted in its entirety in the drawings.

In some embodiments, hard mask layer 102 may include a deposited or thermally formed silicon dioxide-based compound of a thickness in the range of approximately 50 Å to 200 Å. In other embodiments, hard mask layer 102 may include dielectric materials other than a silicon dioxide-based compound such as silicon nitride. These embodiments may be useful for applications in which subsequently formed nanoclusters are made of or have exterior shells of a silicon dioxide-containing material. In this situation, it may be desirable to have a non-oxide hard mask layer 102 to improve etch selectivity with respect to the nanoclusters.

Figure 2:
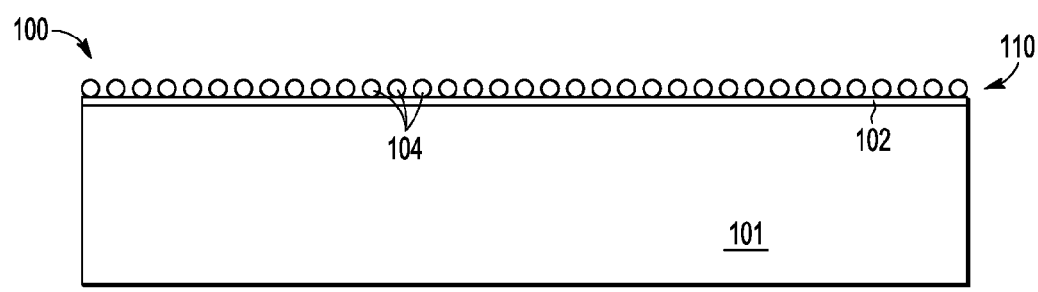
FIG. 2 shows first nanoclusters formed on the hard mask.

Referring now to FIG. 2, a first nanocluster layer 110 including nanoclusters 104 is formed overlying hard mask layer 102. Although the description provided herein refers primarily to metal nanoclusters and polysilicon nanoclusters, any of a variety of other materials may be used for nanoclusters and the selection of a particular material is an implementation detail.

Nanoclusters 104 can be formed by numerous methods including precipitation, chemical reaction, and self-assembly. Self-assembly includes depositing a thin trapping layer and annealing the film in an inert ambient at a temperature close to the eutectic temperature of the trapping layer. The size of the resulting nanoclusters is influenced by the thickness of the trapping layer and the temperature and duration of the anneal. Nanocluster precipitation includes implanting an insulating layer to create a mixed trapping layer and annealing the mixed trapping layer. Increasing the anneal temperature may increase the density of the nanocluster structures. The chemical reaction method includes forming a binary or tertiary mixed layer using one or more material systems. The mixed layer is then subjected to a rapid thermal anneal in an oxygen-bearing ambient.

To illustrate a nanocluster formation process, nanoclusters may be formed by chemical vapor deposition using silane or disilane as a precursor. The width and spacing may be controlled by controlling the deposition temperature and the process time. Nanoclusters can be made larger by increasing the deposition time and can be spaced wider apart by increasing the temperature of the deposition. In one embodiment where the nanoclusters are silicon, the nanoclusters are formed by a chemical vapor deposition process at a temperature of 450-500° C. and a time at temperature of 50-250 seconds to provide silicon nanoclusters having an average width of 10 nm and an average spacing of 12 nm.

Regardless of the specific process used in the formation of first nanocluster layer 110, the process parameters are controlled to achieve a nanocluster layer exhibiting a first set of nanocluster characteristics including, as examples, an average diameter characteristic indicative of an average diameter of nanoclusters 104, and a density characteristic indicative of the density of nanoclusters 104. Other characteristics of nanocluster layer 110 may also be specified and monitored.

Figure 3:
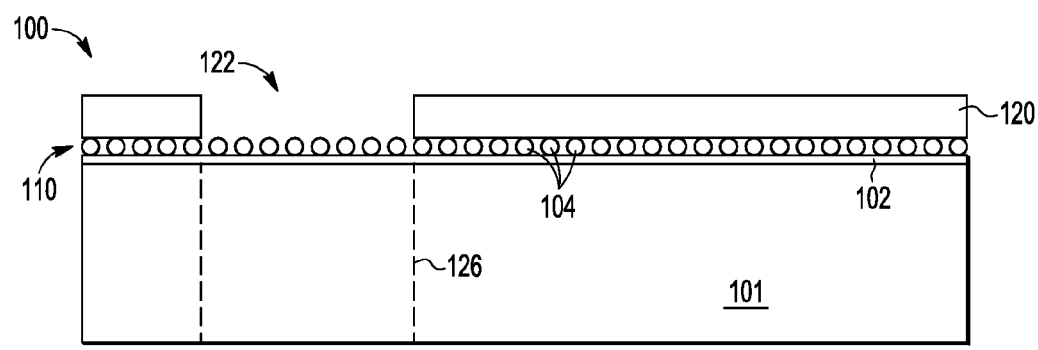
FIG. 3 shows a photoresist window opened over a first nanopillar region.

Referring now to FIG. 3, a photoresist layer 120 is formed overlying first nanocluster layer 110 and patterned to open a window 122 in photoresist layer 120 overlying first region 126 of substrate 101. First region 126 represents a portion of substrate 101 that will include nanopillars having a first set of characteristics while a second region will include nanopillars having a second set of characteristics as described and depicted with respect to FIG. 7 below.

Figure 4:
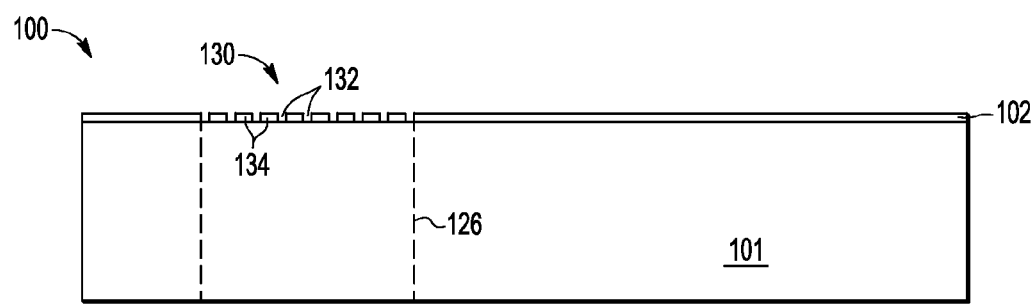
FIG. 4 shows the hard mask patterned through the nanoclusters.

Referring now to FIG. 4, a first nanopillar pattern 130 is formed in hard mask layer 102 by etching hard mask layer 102 using first nanocluster layer 110 (FIG. 3) as a mask. Using nanocluster layer 110 as an etch mask results in first nanocluster pattern 130 including a plurality of nanopillar openings 132 defining a plurality of filler elements 134 formed in hard mask layer 102. The sizes and locations of filler openings 132 reflect the sizes and locations of nanoclusters 104 in first nanocluster layer 110.

The etching of hard mask layer 102 may include a wet etch process, a dry etch process, or a combination thereof. The etch or set of etches used preferably exhibits high selectivity with respect to hard mask layer 102 and nanoclusters 104 and with respect to hard mask layer 102 and substrate 101. For example, in embodiments that employ a silicon dioxide-based hard mask layer 102, metal nanoclusters 104, and a silicon substrate 101, hard mask layer 102 may be wet etched with an HF solution, dry etched using a suitable silicon dioxide plasma etch, or a combination thereof.

In embodiments that use a semiconductor nanocluster such as a silicon nanocluster for nanocluster layer 110, suitable etch selectivity can be achieved with respect to substrate 101 and hard mask layer 102 by using different materials for hard mask layer 102 and/or substrate 101. Hard mask layer 102 may, for example, include a silicon nitride layer. If the substrate is silicon, etch selectivity may be achieved by oxidizing an outer shell of nanoclusters 104 and then employing a silicon nitride etch.

Figure 5:
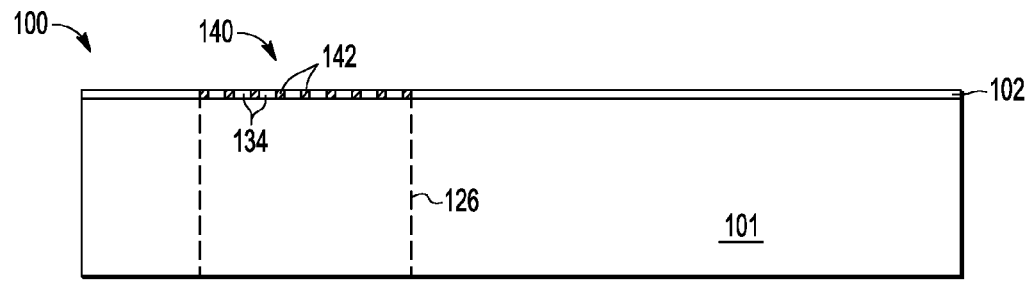
FIG. 5 shows passivation formed in the hard mask openings

Referring now to FIG. 5, a filler material is introduced in the nanopillar openings 132 (see FIG. 4) of first pattern 130 to form filler elements 142. Filler elements 142 preferably exhibit high etch selectivity with respect to hard mask layer 102. For embodiments in which hard mask layer 102 is a silicon dioxide-based compound, filler elements 142 may be silicon nitride or another material that can be etched selectively with respect to hard mask layer 102. The formation of filler elements 142 may include any of various deposition techniques including various chemical vapor deposition techniques and spin-on techniques. The formation of filler elements 142 may further include one or more etch or polishing steps such as chemical mechanical polishing (CMP) steps. As depicted in FIG. 5, hard mask layer 102 overlying substrate 101 includes a first nanopillar pattern 140 overlying a first region 126 of substrate 101. First pattern 140 as depicted in FIG. 5 includes a plurality of filler elements 142 formed in hard mask layer 102 where the size, location, and density of filler elements 142 reflect the size, location, and density of nanocluster layer 110 described above.

Figure 6:
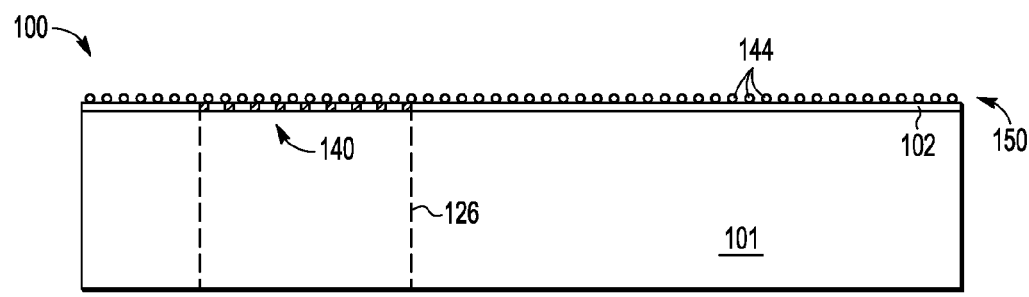
FIG. 6 shows second nanocluster formation.
Figure 7:
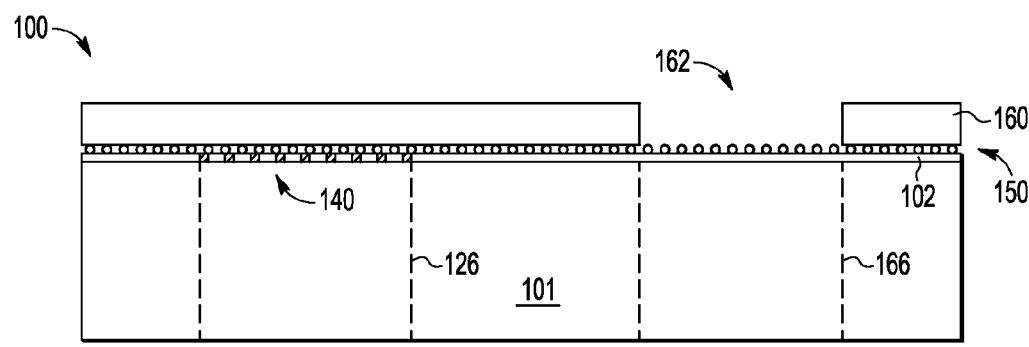
FIG. 7 shows a photoresist mask opened over a second nanopillar region.
Figure 8:
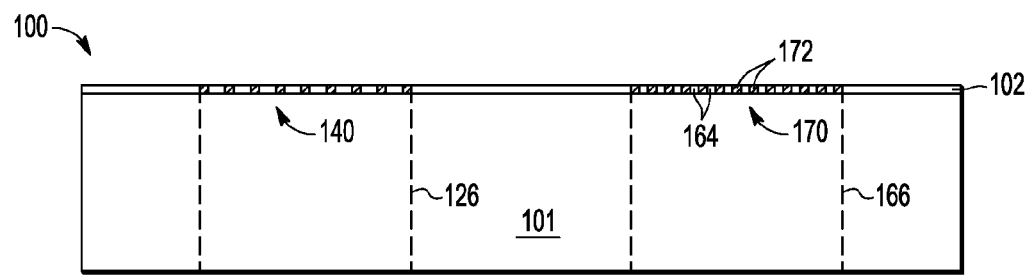
FIG. 8 shows the hard mask after patterning through the second nanoclusters.

Referring now to FIG. 6-FIG. 8, a sequence of processing steps is performed to produce a second pattern 170 (FIG. 8) in hard mask layer 102 overlying a second region 166 of substrate 101. As depicted in FIG. 6, a second nanocluster layer 150 is formed overlying hard mask layer 102. The second nanocluster layer 150 includes nanoclusters 144 characterized by a second nanocluster density and a second average nanocluster diameter. To facilitate a hybrid nanopillar device, the density and/or average diameter for nanoclusters 144 may differ from the density and/or average diameter of nanoclusters in first nanocluster layer 110 described previously.

The density and average diameter of nanoclusters 144 in second nanocluster layer 150 may be controlled through any one or more parameters of the nanocluster deposition process used to deposit second nanocluster layer 150. For example, the formation of second nanocluster layer 150 may include a deposition process that is similar or substantially similar to the process used to deposit first nanocluster layer 110, but wherein one or more deposition parameters may be different than the nanocluster formation process used to produce first nanocluster layer 110 as depicted in FIG. 2. Thus, the second nanoclusters 144 may be of the same material as first nanoclusters 104 and may be formed using the same deposition equipment, varying only one or more deposition parameters to achieve different densities and sizes of nanoclusters. Depending upon the deposition processes employed, the parameters that might be varied include deposition temperatures, pressures and partial pressures, duration, precursors, flow rates, energy fields, anneal temperatures, and so forth.

An example illustrating how changing the value of a nanocluster fabrication process parameter can affect a characteristic of the resulting nanoclusters was described above with respect to FIG. 2 for silicon nanoclusters, but analogous results can be observed for other types of nanoclusters such as metal nanoclusters. For example, applicable literature suggests that changing the anneal temperature from 650° C. to 750° C. in a process for forming nickel nanoclusters on hafnium dioxide using an ammonium anneal can increase the average diameter of the nanoclusters from approximately 19.5 nm to 21.7 nm, representing a change of approximately 5% to 15%. Similarly, the same change in anneal temperature may reduce the nanocluster density from approximately $8E10/cm^2$ for 650° to $4E10/cm^2$, representing a change of approximately 25% to 60%.

In other embodiments, second nanoclusters 144 may be of a different material than first nanoclusters 104 and may have been formed using a different deposition process than the process used to form first nanoclusters 104.

Referring now to FIG. 7, a photoresist layer 160 is formed overlying second nanocluster layer 150 and an opening 162 is formed in photoresist layer 160 overlying a second region 166 of substrate 101. In the embodiment depicted in FIG. 7, the second region 166 of substrate 101 is laterally displaced from first region 126 of substrate 101 such that, there is no overlap between the two regions.

Referring now to FIG. 8, second nanopillar pattern 170 is formed in hard mask layer 102 overlying second region 166 of substrate 101. The formation of filler elements 172 may be the same as or similar to the formation of filler elements 142 described with respect to FIG. 5 and any of various deposition techniques including various chemical vapor deposition techniques and spin-on techniques. The formation of filler elements 172 may further include one or more etch or CMP or other polishing steps. The second nanopillar pattern 170 includes a plurality of filler elements 164 formed in hard mask layer 102. Second pattern 170 is formed in hard mask layer 102 by etching hard mask layer 102 using second nanocluster layer 150 and second photoresist layer 160 as masks so that the portions of hard mask layer 102 etched are determined by the density and position of second nanoclusters 164 within the window 162 of second photoresist layer 160.

Figure 9:
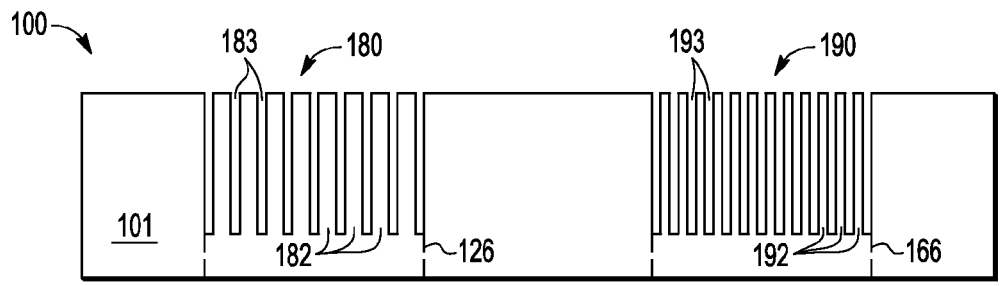
FIG. 9 shows the first and second sets of nanopillars formed by etching the substrate through the patterned hard mask.

Referring now to FIG. 9, processing subsequent to FIG. 8 is depicted. FIG. 9 depicts a first nanopillar set 180 has been formed in first region 126 of substrate 101 and a second nanopillar set 190 has been formed in second region 166 of substrate 101. First nanopillar set 180 includes a first set of nanopillars 182 having a first density, a first average diameter, and other characteristics. Second nanopillar set 190, similarly includes a second set of nanopillars 192 having a second density, a second average diameter, and a second set of other characteristics.

In some embodiments, the formation of first nanopillar set 180 and the formation of second nanopillar set 190 both occur during a single processing sequence following the processing depicted in FIG. 8. For example, after the processing depicted in FIG. 8, filler elements 172 (FIG. 8) and 142 (FIG. 5) are removed and substrate 101 is etched. Because the material for hard mask layer 102 differs from the material of substrate 101, an etch that is highly selective with respect to substrate 101 is employed to form first nanopillar cavities 183 in first region 126 and second nanopillar cavities 193 in second region 166 of substrate 101.

For implementations in which substrate 101 is primarily comprised of silicon or another semiconductor substrate and hard mask layer 102 is primarily comprised of silicon dioxide or another dielectric compound, the formation of first nanopillar set 180 and second nanopillar set 190 may include performing a silicon etch using, in some embodiments, an anisotropic etch process. Depending upon the implementation, nanopillars 182 and 192 may have an aspect ratio that exceeds, for example, 10 to 1.

Figure 10:
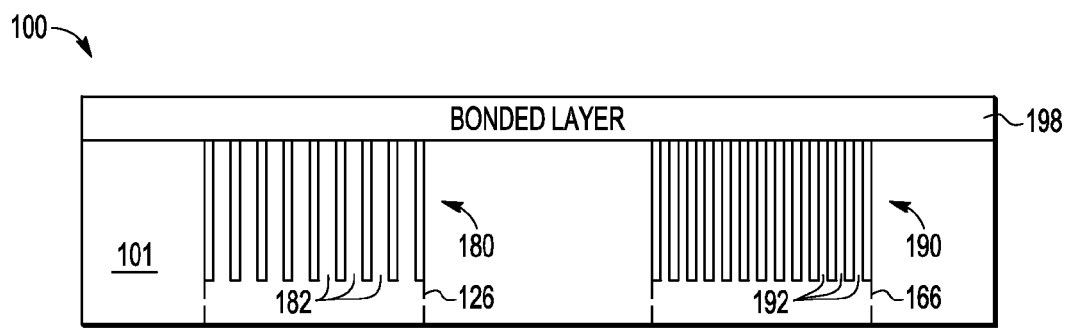
FIG. 10 shows a bonded layer formed overlying the tops of the nanopillars.

Turning now to FIG. 10, processing subsequent to the processing depicted in FIG. 9 is depicted in which a bonded layer 199 is formed overlying substrate 101. In some embodiments, bonded layer 199 includes a silicon substrate bonded onto the underlying substrate 101. The thickness of bonded layer 199 may be in the range of approximately 100 to 1000 microns.

In some embodiments, the formation of bonded layer 199 may include bonding a handle wafer that includes bonded layer 199 to a device wafer that includes semiconductor substrate 101. The method of bonding may include thermal bonding, adhesive bonding, anodic bonding, or another form of bonding suitable for use in a semiconductor fabrication environment. Bonded layer 199 may include one or more dielectric layers such as silicon dioxide-based layers, one or more silicon or other semiconductor layers, or a combination of thereof. As depicted in FIG. 10, bonded layer 199 caps nanopillar cavities 183 and 193, which were previously opened to the environment. For the use of nanopillar devices in certain applications including, for example, environmental monitoring applications, in which it is necessary or desirable to expose nanopillars 182 and 192 to the environment, bonded layer 199 may be omitted.

Figure 11:
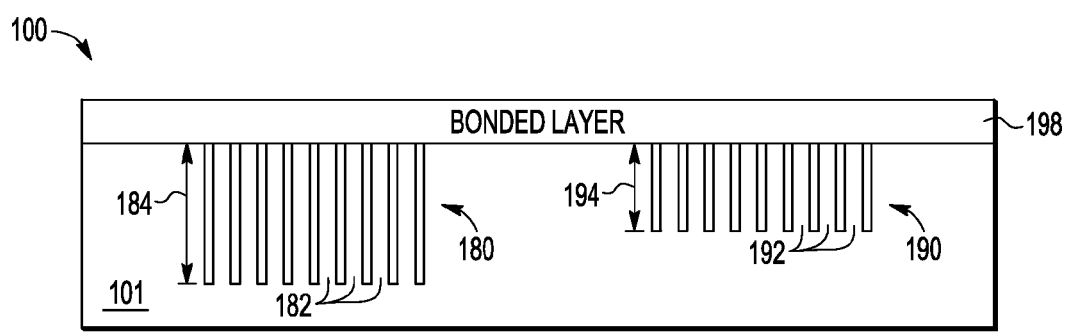
FIG. 11 shows a possible feature in which two nanopillar etches are performed to achieve two different nanopillar heights.

Referring now to FIG. 11, an embodiment of alternative and optional processing subsequent to FIG. 9 is depicted in which the first nanopillar set 180 is formed having a greater depth or aspect ratio then second nanopillar set 190. In this embodiment, separate etch steps may be used to form first nanopillars 182 and second nanopillars 192. For example, a first etch process may be used to form first nanopillars 182 having a first depth represented by reference numeral 184. The second nanopillars 192 may be formed with a second etch process to achieve a second depth indicated by reference numeral 194. In the embodiments depicted in FIG. 11, differentiation between first nanopillar set 180 and second nanopillar set 190 may refer to the different depths 184, 194 of the respective nanopillars 182, 192. Additionally, nanopillar sets 180 and 190 may also have different densities and/or sizes.

Figure 12:
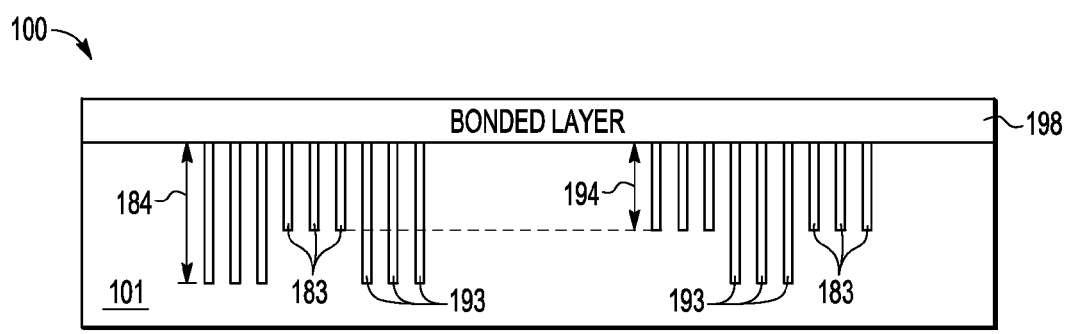
FIG. 12 shows a variation of FIG. 11 in which each nanocluster region includes two different nanopillar heights.

In FIG. 12, an alternative to the embodiment of FIG. 11 is shown in which some of the first nanopillar voids 183 and some of the second nanopillar voids 193 have a depth 194 while other of first nanopillar voids 183 and second nanopillar voids 193 have a depth 184.

Figure 13:
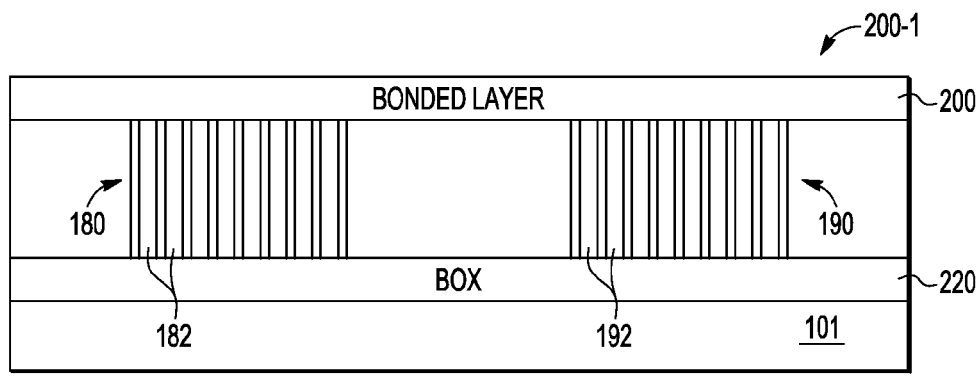
FIG. 13 shows an SOI implementation in which nanopillars sit on a buried oxide layer.

Turning now to FIG. 13 through FIG. 19, selected embodiments of a hybrid nanopillar device 200-1 to 200-6, any one or more of which may be referred to generically as hybrid nanopillar device(s) 200, are depicted. Each of the depicted embodiments of hybrid nanopillar device 200 includes two or more sets of nanopillars and may include a device structure for conveying an input signal or input medium to the nanopillars, a device structure for monitoring the nanopillars, or both. FIG. 13, for example, depicts an embodiment of hybrid nanopillar device 200-1 having a semiconductor on insulator substrate 101 that includes a buried oxide layer 220 overlying a bulk portion of substrate 101. As depicted in FIG. 13, first nanopillar set 180 and second nanopillar set 190 are formed between buried layer 220 and bonded layer 199, which may itself include or consist primarily of a dielectric material, a semiconductor material such as silicon, or a combination of the two. It will be appreciated by one of skill in the field of semiconductor fabrication that, if bonded layer 199 is an electrical insulator, individual nanopillars in first nanopillar set 180 and second nanopillar set 190 are electrically isolated from one another with no conductive material line between them. Although FIG. 13 does not depict structures for conveying an input signal or medium to the nanopillars or a structure to monitor the nanopillars, the depicted embodiment may be suitable for applications in which the electrical isolation of nanopillars 182 and 192 may be desirable.

Figure 14:
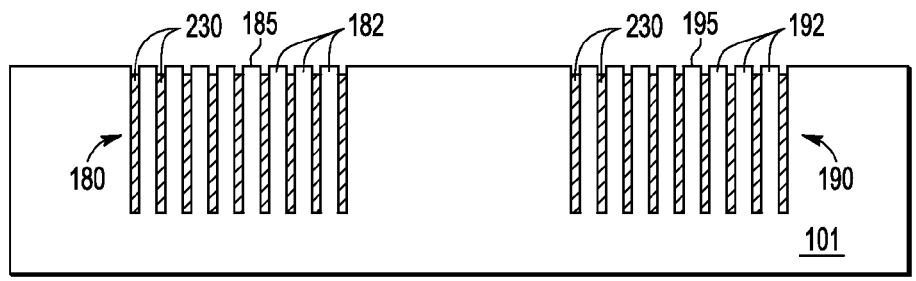
FIG. 14 and FIG. 15 show the formation of an epitaxial top layer by depositing oxide or the like in the nanopillar trenches, leaving tips of the nanopillars exposed, and subsequently performing epitaxial growth.
Figure 15:
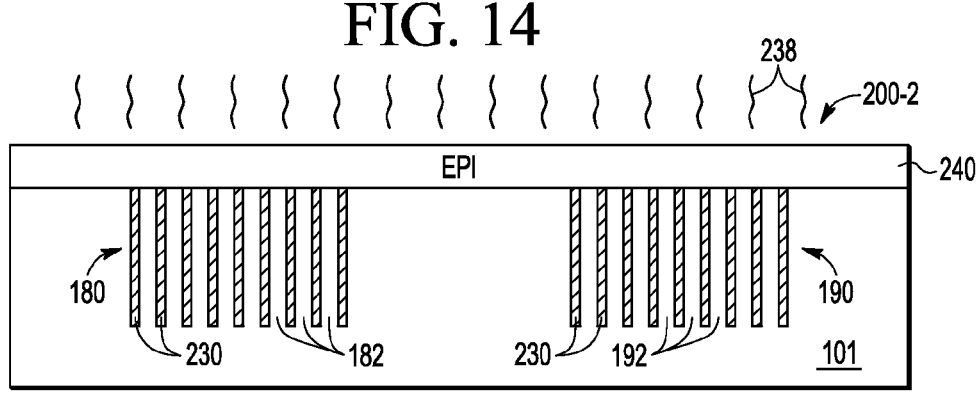

Referring now to FIG. 14 and FIG. 15, depicting processing subsequent to that depicted in FIG. 9, a dielectric material 230 is formed to fill cavities between adjacent first nanopillars 182, and cavities between adjacent second nanopillars 192.

The dielectric material 230 may, for example, be any material that is suitable for suppressing epitaxial growth of a film on silicon substrate 101. A suitable material for dielectric 230 may include, for example, silicon nitride. The deposition of dielectric material 230 may continue until nanopillars 182 and 192 are enveloped in dielectric for most, but not all, of their height. Peripheral or extreme portions of nanopillars 182 and 192 remain exposed after formation of the dielectric material 230. For example, one implementation may deposit dielectric material 230 to cover approximately 80 to 95% of nanopillars 182 and 192 leaving only extreme portions 185 and 195 of nanopillars 182 and 192 exposed.

Referring now to FIG. 15, thermal processing represented by reference numeral 238 is performed to grow a substantially uniform epitaxial film 240 overlying substrate 101 to form hybrid nanopillar device 200-2. Depending upon the implementation, dielectric material 230 may include some form of silicon dioxide or silicon nitride material. In the embodiment depicted in FIG. 15, epitaxial layer 240 may be a homoepitaxy layer in which epitaxial layer 240 comprises substantially the same material as substrate 101. In other embodiments, the epitaxial formation depicted may include a heteroepitaxy process in which layer 240 comprises a different material than substrate 101. For example, epitaxial layer 240 may include a conductive or insulating layer fabricated over a single crystalline layer.

Figure 16:
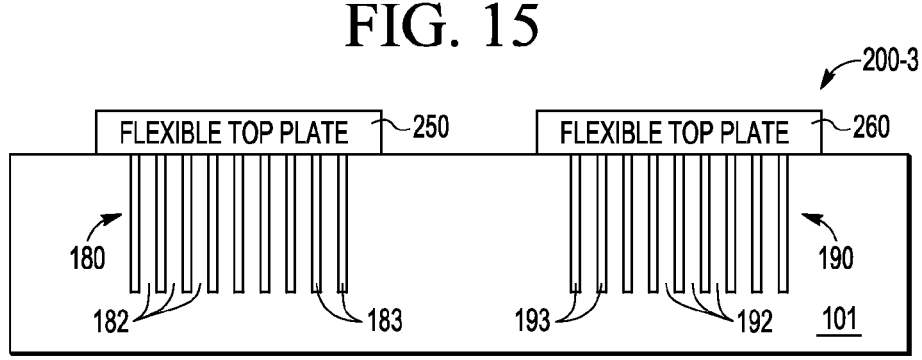

Referring to FIG. 16, an embodiment of hybrid nanopillar device 200-3 is depicted in which flexible top plates 250 and 260 are formed respectively overlying first nanopillar set 180 and second nanopillar set 190. In some embodiments, flexible top plate 250 may be a part of the same flexible top plate as flexible top plate 260. In other embodiments, the two top plates 250 and 260 are distinct. Flexible top plates 250 and/or 260 may include a flexible and electrically conductive top plate or top plates overlying substrate 101. In these embodiments, the one or more flexible top plates 250, 260, could be used to enable, for example, a piezoresistive sensor such as a tire pressure monitor. In this embodiment, small changes in pressure outside the sensor may alter electrical or physical characteristics of first nanopillars 182 and/or second nanopillars 192.

Figure 17:
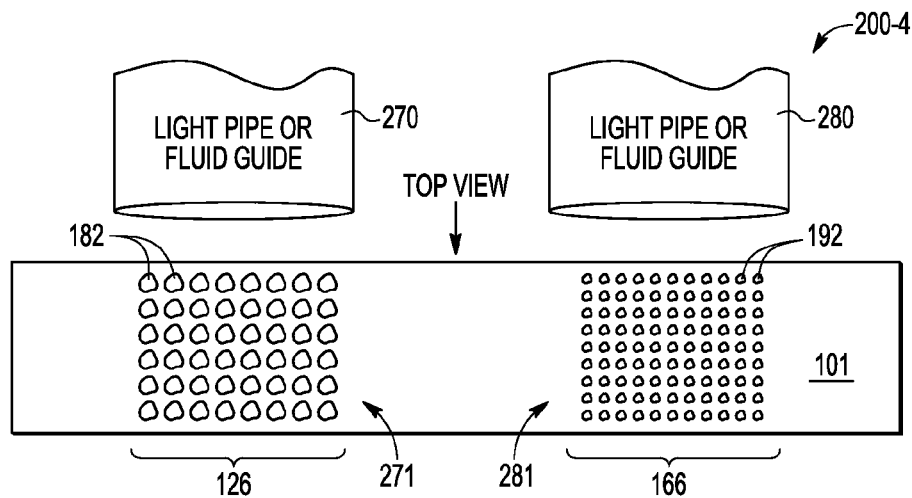
FIG. 17 is a top view of the substrate and includes light pipes or fluid guides to guide light or fluid through a filtering, sensing, or polarizing array of nanopillars.

Referring now to FIG. 17, an embodiment of hybrid nanopillar device 200-4 includes one or more light pipes or fluid guides 270, 280, for use in funneling or otherwise guiding light or liquid to regions 126, 166 of substrate 101 that include first and second arrays 271, 281 of nanopillars 182, 192. As depicted in FIG. 17, substrate 101 is shown in top view and nanopillar arrays 271, 281 extend from a first sidewall of substrate 101 to a second sidewall. Although FIG. 17 depicts nanopillars 182, 192 as being arranged in arrays 271, 281 with strictly ordered rows and columns, it will be appreciated by those of skill in the art of nanocluster formation that nanopillar arrays 271, 281 may exhibit a random or less regular arrangement of nanopillars 182, 192. In addition, while FIG. 17 illustrates two distinct light pipes or fluid guides 270, 280, other implementations may employ a single light pipe or fluid guide that conveys the light or fluid to first and second regions 126, 166 of substrate 101.

Figure 18:
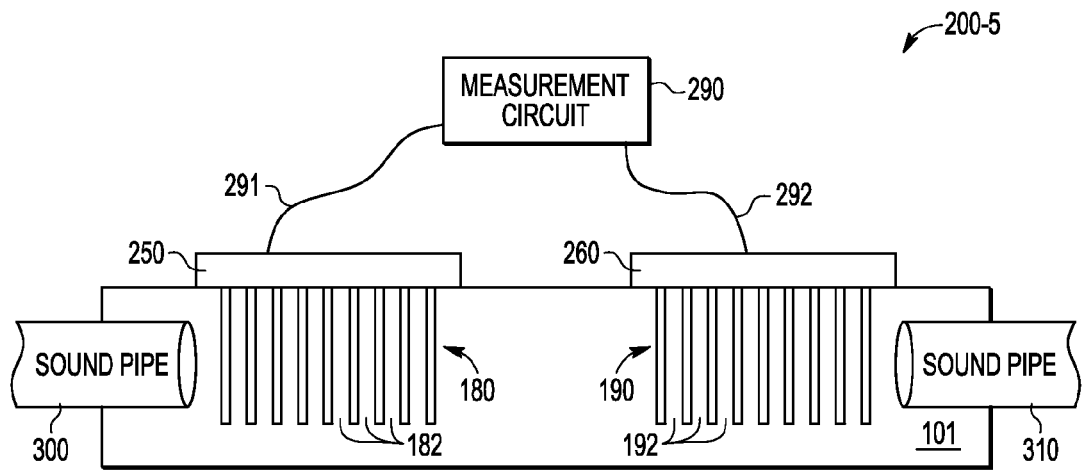
FIG. 18 shows conveying sound to the nanopillar regions in conjunction with measuring circuitry to monitor the resistance or other parameters of the nanopillars.

Referring now to FIG. 18, an embodiment of apparatus 200-5 is depicted to illustrate the inclusion of nanopillar sets 180, 190, formed in substrate 101 in a sound detection device. In the embodiment depicted in FIG. 18, for example, sound pipes 300 and 310 are depicted conveying sound through openings in semiconductor substrate 101 to regions of substrate 101 that include first and second nanopillar sets 180, 190. In the depicted embodiment, apparatus 200-5 includes a first flexible top plate 250 formed on or in contact with nanopillar set 180 and a second flexible top plate 260 formed on or in contact with nanopillar set 190. Measurement circuit 290 includes an interconnection 291 to top plate 250 for sensing parameters associated with first nanopillar set 180. Measurement circuit 290 further includes an interconnection 292 to top plate 260 for sensing parameters associated with second nanopillar set 192. Measurement circuit 290 may use Interconnections 292 to identify differences in pressure, resistance, temperature, or other parameters of nanopillars 182, 192 and any such detected differences in parameter values may be used to identify, for example, sound in a hearing aid or other type of audio application. Although the circuitry shown in conjunction with substrate 101 in FIG. 18 is a measuring circuit 290, other circuits may be employed in conjunction with substrate 101.

Figure 19:
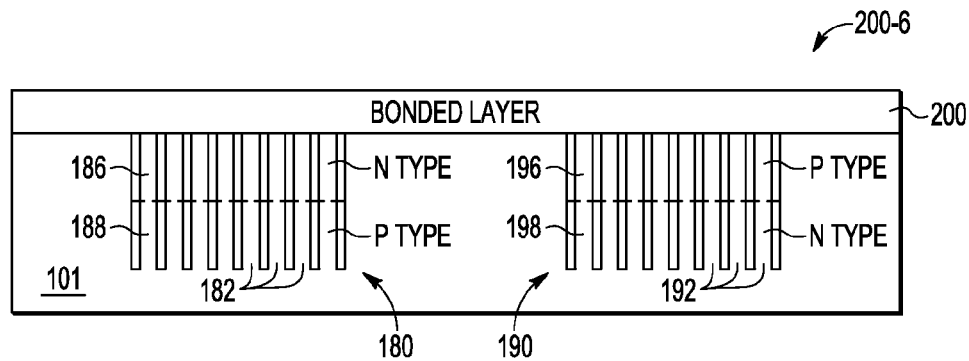
FIG. 19 shows pillars having n-p and/or p-n junctions.

Yet another example of an apparatus 200-6 is depicted in FIG. 19 in which a first portion 186 of one or more nanopillars 182 is doped n-type while a second portion 188 of the same one or more nanopillars 182 is doped p-type. FIG. 19 further depicts a first portion 196 of one or more nanopillars 192 is doped p-type while a second portion 198 of the same one or more nanopillars 192 is doped n-type. In either of these implementations, it will be appreciated that each nanopillar 182, 192 includes a p-n junction and that the corresponding nanopillar may be used to implement for example, diode structures that may be used in light emitting diodes and other applications. In these embodiments, the light emitting diode structures may include a material suitable for generating photons in the visible frequency as well as a phosphor material that is excited by the released photons.

Although FIG. 19 depicts all of the first nanopillars 182 having a common p-n junction structure and all of second nanopillars 192 having a common p-n junction structure that is different than the p-n junction structure of first nanopillars 182, other embodiments may include, as an example, a common p-n junction structure for all nanopillars 182, 192.

In addition to the structures and implementations of hybrid nanopillar devices 100 depicted in the drawings, other features and applications for hybrid nanopillar devices include applying a voltage to a top plate and/or a bottom plate to implement an electrostatic filter. In another implementation, nanopillars 182 and 192 may be coated with reactive agents to facilitate biological or chemical sensing. Nanopillars 182 and 192 could be formed from or fabricated to include a magnetic material to produce magnetic nanopillars to enable a magnetic fluid filter, for example. A glass or other form of insulating plate could be bonded to the top of the nanopillars. For example, as depicted in FIG. 13, bonded layer 199 may include a glass or oxide plate in contact with nanopillars 182 and 192. The use of a glass plate could provide isolation at the top of each nanopillar 182 and 192, for electrostatic filter applications that might need an applied voltage without a current flow.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements.

What is claimed is:

1. A method of fabricating a nanopillar device, the method comprising:
    forming a mask layer on a substrate;
    forming a first layer of nanoclusters over the mask layer;
    patterning a first layer of photoresist over the first layer of nanoclusters to open a window overlying a first region of the substrate;
    using the first layer of photoresist and the first layer of nanoclusters as an etch mask, etching a first region of the mask layer overlying the first region of the substrate to transfer a pattern formed by the first layer of nanoclusters into the first region of the mask layer;

after removing the first layer of photoresist and the first layer of nanoclusters, forming a second layer of nanoclusters over the mask layer; and patterning a second layer of photoresist over the second layer of nanoclusters to open a window overlying a second region of the substrate;

using the second layer of photoresist and the second layer of nanoclusters as an etch mask, etching a second region of the mask layer overlying the second region of the substrate to transfer a pattern formed by the second layer of nanoclusters into the second region of the mask layer; and etching the substrate through the mask layer to form a first set of nanopillars in the first region of the substrate and a second set of nanopillars in the second region of the substrate.

2. The method of claim 1, wherein an average of a characteristic of the first set of nanopillars differs from an average of the characteristic for the second set of nanopillars.

3. The method of claim 2, wherein the characteristic is average nanopillar density.

4. The method of claim 3, wherein a difference between the nanopillar density of the first set of nanopillars and the nanopillar density of the second set of nanopillars is in the range of approximately 25% to approximately 60%.

5. The method of claim 2, wherein an average diameter of the first set of nanopillars differs from an average diameter of the second set of nanopillar.

6. The method of claim 5, wherein the average diameter of the first set of nanopillars differs from the average diameter of the second set of nanopillars by a percentage difference in the range of approximately 5% to approximately 15%.

7. The method of claim 2, wherein the first set of nanopillars is comprised of a different material than the second set of nanopillars.

8. The method of claim 1, further comprising:

filling cavities between nanopillars with a filler dielectric, wherein the filling of the cavities leaves extremities of the nanopillars exposed; and growing an epitaxial film on the extremities of the nanopillars.

9. The method of claim 1, forming a flexible and electrically conductive top plate overlying the first set of nanopillars to implement a piezoresistive sensor.

* * * * *